United States Patent
Hugo et al.

(10) Patent No.: US 7,528,284 B2
(45) Date of Patent: *May 5, 2009

(54) METHOD FOR PRODUCING XYLYLENEDIAMINE (XDA)

(75) Inventors: Randolf Hugo, Dirmstein (DE); Sabine Jourdan, Mannheim (DE); Kirsten Wenz, Mannheim (DE); Thomas Preiss, Weisenheim am Sand (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/571,425

(22) PCT Filed: Sep. 4, 2004

(86) PCT No.: PCT/EP2004/009884

§ 371 (c)(1),
(2), (4) Date: Feb. 12, 2007

(87) PCT Pub. No.: WO2005/026103

PCT Pub. Date: Mar. 24, 2005

(65) Prior Publication Data

US 2008/0091049 A1 Apr. 17, 2008

(30) Foreign Application Priority Data

Sep. 10, 2003 (DE) ................. 103 41 633

(51) Int. Cl.
*C07C 209/00* (2006.01)

(52) U.S. Cl. ..................................................... 564/415
(58) Field of Classification Search .................. 564/415
See application file for complete search history.

(56) References Cited

U.S. PATENT DOCUMENTS 7,323,598 B2 * 1/2008 Hugo et al. ................. 564/415

FOREIGN PATENT DOCUMENTS

| EP | 1 193 244 | 4/2002 |
| EP | 1 279 661 | 1/2003 |
| WO | WO 2005/028417 A1 | 3/2005 |

OTHER PUBLICATIONS

International Search Report No. PCT/EP2004/009568 dated Nov. 23, 2004, 6 pages.

* cited by examiner

*Primary Examiner*—Jafar Parsa
(74) *Attorney, Agent, or Firm*—Connolly Bove Lodge & Hutz LLP

(57) ABSTRACT

A process for preparing xylylenediamine, comprising the steps of ammoxidizing xylene to phthalonitrile and hydrogenating the phthalonitrile, which comprises contacting the vaporus product of the ammoxidation stage directly with a liquid organic solvent or with molten phthalonitrile (quench), partly or fully removing components having a boiling point lower than phthalonitrile (low boilers) from the resulting quench solution or suspention or phthalonitrile melt and, before the hydrogenation, of the phthalonitrile, not removing any products having a boiling point higher than phthalonitrile (high boilers).

20 Claims, 3 Drawing Sheets

BN = Benzonitrile
TN = Tolunitrile

METHOD FOR PRODUCING XYLYLENEDIAMINE (XDA)

CROSS REFERENCE TO RELATED APPLICATION

The present application is a national stage application of PCT/EP2004/009884, filed Sep. 4, 2004, which claims priority from German Patent Application No. DE 103 41 633.1, filed Sep. 10, 2003.

The present invention relates to a process for preparing xylylenediamine, comprising the steps of ammoxidizing xylene to phthalonitrile and hydrogenating the phthalonitrile.

Xylylenediamine (bis(aminomethyl)benzene) is a useful starting material, for example for the synthesis of polyamides, epoxy hardeners or as an intermediate for preparing isocyanates.

The term "xylylenediamine" (XDA) comprises the three isomers ortho-xylylenediamine, meta-xylylenediamine (MXDA) and para-xylylenediamine.

The term "phthalonitrile" (PN) comprises the three isomers, 1,2-dicyanobenzene=o-phthalonitrile, 1,3-dicyanobenzene=isophthalonitrile=IPN and 1,4-dicyanobenzene =terephthalonitrile.

The two-stage synthesis of xylylenediamine by ammoxidizing xylene and subsequently hydrogenating the resulting phthalonitrile is known.

EP-A2-1 113 001 (Mitsubishi Gas Chem. Comp.) describes a process for preparing nitrite compounds by ammoxidizing corresponding carbocyclic or heterocyclic compounds, in which excess ammonia from the reaction product is recycled. Also described is the direct contacting of the vaporous product of the ammoxidation stage with a liquid organic solvent which is in particular aliphatic or aromatic hydrocarbons (paragraphs [0045] and [0046]).

EP-A2-1 193 247 and EP-A1-1 279 661 (both Mitsubishi Gas Chem. Comp.) relate to a process for purifying isophthalonitrile (IPN) and to a process for preparing pure XDA respectively, in which the phthalonitrile is synthesized by ammoxidizing xylene, and the vaporous product of the ammoxidation stage is contacted directly with a liquid organic solvent (quench).

The organic solvent is selected from alkylbenzenes, heterocyclic compounds, aromatic nitrites and heterocyclic nitrites, and has a boiling point which is below that of phthalonitrile (EP-A2-1 193 247: column 4, paragraph [0018] and [0019]; EP-A1-1 279 661: columns 4-5, paragraph [0023] and [0024]).

EP-A2-1 193 244 (Mitsubishi Gas Chem. Comp.) describes a process for preparing XDA by hydrogenating phthalonitrile which is synthesized in a preceding stage by ammoxidizing xylene, in which the vaporous product of the ammoxidation stage is contacted directly with a liquid organic solvent (quench) and the resulting quench solution or suspension is fed to the hydrogenation.

Preferred organic solvents are $C_6$-$C_{12}$ aromatic hydrocarbons such as xylene and pseudocumene (column 6, paragraph [0027] and [0028]).

DE-A-21 64 169 describes, on page 6, last paragraph, the hydrogenation of IPN to meta-XDA in the presence of an Ni and/or Co catalyst in ammonia as a solvent.

Five parallel BASF patent applications each having the same application date each relate to processes for preparing XDA.

It is an object of the present invention to provide an improved, economically viable process for preparing highly pure xylylenediamine, in particular meta-xylylenediamine, with high yield and space-time yield (STY), which, at comparable throughputs to prior art processes (for example EP-A2-1 193 244, EP-A1-1 279 661), enables smaller and/or fewer apparatus and machines as a consequence of reduced streams, in particular solvent streams, including recycle streams.

We have found that this object is achieved by a process for preparing xylylenediamine, comprising the steps of ammoxidizing xylene to phthalonitrile and hydrogenating the phthalonitrile, which comprises contacting the vaporous product of the ammoxidation stage directly with a liquid organic solvent or with molten phthalonitrile (quench), partly or fully removing components having a boiling point lower than phthalonitrile (low boilers) from the resulting quench solution or suspension or phthalonitrile melt and, before the hydrogenation, of the phthalonitrile, not removing any products having a boiling point higher than phthalonitrile (high boilers).

The process according to the invention preferably finds use for preparing meta-xylylenediamine (MXDA) by hydrogenating isophthalonitrile (IPN) which is synthesized in a preceding stage by ammoxidizing meta-xylene.

The process according to the invention can be performed as follows:

Ammoxidation Stage:

The ammoxidation of xylene (o-, m- or p-xylene) to the corresponding phthalonitrile (ortho-xylene→o-phthalonitrile; meta-xylene→isophthalonitrile; para-xylene→terephthalonitrile) is generally carried out by processes known to those skilled in the art.

The ammoxidation of methyl aromatics is preferably carried out over a multioxide catalyst with ammonia and an oxygenous gas (oxygen or air or both) in a fluidized bed reactor or a tube (bundle) reactor.

The reaction temperature is generally from 300 to 500° C., preferably from 330 to 480° C.

The catalyst preferably comprises V, Sb and/or Cr and is more preferably composed of [V, Sb and alkali metals] or [V, Cr, Mo and B], in each case as an unsupported catalyst or on an inert support.

Preferred inert supports are $SiO_2$, $Al_2O_3$ or a mixture of both, or steatite.

Such a procedure is described, for example, in the BASF patent applications EP-A-767 165 and EP-A-699 476, which are explicitly incorporated herein by way of reference.

The BASF patent applications EP-A-222 249, DE-A-35 40 517 and DE-A-37 00 710 also disclose suitable ammoxidation catalysts.

The ammoxidation may also be carried out in accordance with the processes described in the applications cited at the outset, EP-A2-1 113 001, EP-A2-1 193 247, EP-A1-1 279 661 and EP-A2-1 193 244.

Quench:

The vapor produced in the ammoxidation, comprising the product of value, phthalonitrile, is contacted directly with a liquid organic solvent or with liquid, i.e. molten, phthalonitrile (preferably that isomer which corresponds to the synthesized PN) (quench with a liquid organic solvent or with molten phthalonitrile as a quench liquid, quenching agent).

The organic solvent used for the quench may already comprise dissolved or suspended phthalonitrile (preferably that isomer which corresponds to the synthesized PN).

Preferred organic solvents for the quench are selected from the group of aromatic hydrocarbons (in particular alkylaromatics, very particularly alkylbenzenes), heterocyclic compounds, aromatic nitrites and heterocyclic nitrites and mixtures thereof.

Examples of such solvents which can be used are o-xylene, m-xylene, p-xylene, pseudocumene, mesitylene, ethylbenzene, methylpyridine, benzonitrile, m-tolunitrile, o-tolunitrile, p-tolunitrile, N-methyl-2-pyrrolidone (NMP), THF, methanol and 1,4-dioxane.

Particularly preferred organic solvents are tolunitrile, benzonitrile and NMP and mixtures thereof.

The organic solvent for the quench has a lower boiling point than the synthesized PN (at the same pressure).

The sudden temperature reduction when contacting the vaporous phthalonitrile with the liquid solvent or with the molten phthalonitrile (quench) reduces the formation of undesired secondary and decomposition products which lead to a reduction in the quality of the phthalonitrile and finally of the XDA.

The vaporous phthalonitrile is absorbed by the quench directly into the liquid organic solvent or the molten phthalonitrile, resulting, in the case of the liquid organic solvent, in a solution and/or a suspension and, in the case of the molten phthalonitrile, in a phthalonitrile melt comprising the synthesized PN.

The organic solvent for the quench or the molten phthalonitrile for the quench may be used as fresh feed having a purity >99% by weight, in particular >99.5% by weight.

Preference is given to using organic solvent recovered from the process or phthalonitrile prepared in the process as quench liquid. The purity here of the quench liquid may also be ≦99% by weight, for example 90-98% by weight, especially when the impurities are substances which are not foreign to the process (i.e., inter alia, water, ammonia, benzonitrile, tolunitrile, xylene, o-, m- or p-methylbenzylamine, benzylamine, xylylenediamine).

The amount of the organic solvent used is generally such that solutions/suspensions are obtained which have a phthalonitrile content of from 15 to 75% by weight, preferably from 25 to 60% by weight.

In the case of molten phthalonitrile as the quenching agent, the amount of molten phthalonitrile used depends substantially on the heat to be removed in the quench.

The vaporous effluent of the ammoxidation, comprising the phthalonitrile (PN), is introduced into the liquid organic solvent or into the molten phthalonitrile in a quench apparatus, for example preferably in a falling-film condenser (thin-film, trickle-film or falling-stream condenser), in a jet apparatus or in a column. In this apparatus, the vaporous phthalonitrile may be conducted in cocurrent or in countercurrent with the liquid solvent or the molten phthalonitrile. In the case of cocurrent flow, the vaporous phthalonitrile is introduced into the quench apparatus from above. It is advantageous to feed the liquid solvent or molten phthalonitrile tangentially at the top of the falling-film condenser or to feed the liquid solvent or molten phthalonitrile through one or more nozzles, in order to achieve complete wetting of the interior wall of the quench apparatus.

To increase the surface area available for condensation, the quench apparatus may be equipped with internals such as trays, structured packings or random packings.

The organic solvent or molten phthalonitrile for the quench may be used in single pass or as circulation medium.

Advantageously, a portion of the quench solution or suspension or phthalonitrile melt is recycled (circulation).

A heat transferor installed in the circuit is used to cool the quench solution or suspension or phthalonitrile melt.

The temperature of the circulation medium and the circuit flow rate are set and adjusted with respect to each other in such a way that the desired temperature in the quench exit is achieved. The smaller the flow rate of the circulation medium, the lower the temperature selected of the circulation medium and vice versa, although solubilities and melting points, and also the hydraulic stress limits of the quench apparatus, have to be taken into account.

The flow rate of the freshly fed organic solvent is dependent upon the quench temperature. It is set in such a way that the desired concentration of the PN solution or suspension is obtained. Since the solubility of PN in the organic solvent rises with increasing temperature, a higher PN concentration in the solvent can be conveyed with increasing quench exit temperature.

The circulation medium or the molten phthalonitrile is fed in together with the fresh solvent or separately, at a suitable point in the quench apparatus.

In general, heating of the organic solvent and/or of the circulation medium used sets the temperature of liquid quench effluent to from 40 to 180° C., preferably from 50 to 120° C., in particular from 80 to 120° C.

In the case of molten phthalonitrile as the quenching agent, heating of the molten phthalonitrile and/or of the circulation medium used sets the temperature of the liquid quench effluent, to from 165 to 220° C., preferably from 180 to 220° C., in particular from 190 to 210° C.

The absolute pressure in the course of quenching is generally from 0.5 to 1.5 bar. Preference is given to operating at slightly elevated pressure.

Xylene, water, $NH_3$, $CO_2$, $N_2$, etc., which are generally present in the vaporous effluent of the ammoxidation are only partly or virtually not dissolved under the quench conditions in the quenching agent (organic solvent or molten phthalonitrile), and are removed from the quench apparatus in predominantly gaseous form.

Partial or complete removal of components having a boiling point lower than phthalonitrile (low boilers) (at the same pressure) from the resulting quench solution or suspension or phthalonitrile melt:

The lower the temperature in the quench step, the higher the proportion of water and secondary components which have a lower boiling point than PN (at the same pressure) (for example benzonitrile, tolunitrile) in the liquid quench effluent.

In the process according to the invention, before the hydrogenation of the phthalonitrile, water and components having a boiling point lower than phthalonitrile (at the same pressure) (low boilers; for example, unconverted xylene, benzonitrile, tolunitrile, each as a heteroazeotrope with water, water, benzonitrile, tolunitrile; listing with increasing boiling point (at the same pressure); and if appropriate also benzylamine, o-, m-, p-methylbenzylamine, xylylenediamines, these amines stemming from recycled solvent from the hydrogenation stage) are partly or fully removed from the resulting quench solution or suspension or phthalonitrile melt. This removal is preferably by distillation.

Preference is given to also partly or fully removing the organic solvent used in the quench in this step as a low boiler.

This removal of the solvent and/or of the low boilers may be effected in one or more evaporator stages connected in series or in a distillation column via the top, while phthalonitrile is removed via the bottom together with products having a boiling point higher than phthalonitrile (high boilers) (at the same pressure).

Preference is given to using a distillation column which is equipped preferably with the customary internals for increasing the separating performance, such as trays, structured or random packings, etc.

The configuration of the column (in particular number of separating stages, feed point, reflux ratio, etc.) may, adapted to the particular composition of the solution or suspension, be carried out by those skilled in the art by methods familiar to them.

Preference is given to operating under reduced pressure, in order to limit the bottom temperature.

In a particular embodiment of the process according to the invention, the quench of the vaporous product of the ammoxidation stage with a liquid organic solvent or with molten phthalonitrile is carried out in a column in such a way that reaction gases and low boilers, including any organic solvent used as a quenching agent, are removed partly or fully via the top and phthalonitrile, together with products having a boiling point higher than phthalonitrile (high boilers) is removed via the bottom. (See FIG. 3).

This particular procedure combines quench and low boiler removal in one stage (one step) and in a specific quench apparatus, a quench column. The circulation method already described above of a portion of the quench column effluent is again particularly advantageous, and it is recycled as a quenching agent preferably into about the middle of the column.

Subsequently, any low boilers still present may be removed fully from the resulting phthalonitrile by evaporation or rectification in a subsequent further step under reduced pressure. It is preferred that no further low boiler removal- is carried out in this procedure, but rather that the resulting PN melts from the combined quench/low boiler removal step are conveyed to the hydrogenation.

The gaseous effluent from the ammoxidation is preferably introduced at the column bottom of the quench column, and the fresh quenching agent (organic solvent) at the top (countercurrent), while the quench column effluent consists of a mixture of solvent and PN or (depending on the temperature selected) is virtually solvent free (cf. FIG. 3). The composition of the quench column effluent is determined by the operating conditions of the quench column (in particular temperature) and the flow rate of the solvent fed in at the top of the quench column.

In the case that PN melt is withdrawn at the bottom of the quench column, the organic solvent introduced at the top of the quench column prevents the PN from being discharged via the top. This organic solvent is thus evaporated and removed virtually completely via the top. The flow rate to be introduced is to be adjusted accordingly.

With regard to the composition of the quench column effluent, the transition from a solution of PN in the organic solvent, obtained at a relatively low bottom temperature of the quench column, and a substantially solvent-free PN melt, obtained at a relatively high bottom temperature of the quench column, is fluid.

The temperatures of the quench column effluent are generally as already described for the quench step.

To obtain a PN melt in the bottom effluent of the quench column, the procedure may be as follows:

The hot reaction gases from the ammoxidation are introduced in the bottom of a quench column, cf. FIG. 3. A portion of the bottom effluent is recycled and, after cooling to from approx. 165 to 180° C., reintroduced at about the middle of the column. It has to be ensured that the temperature does not go below the melting temperature. The flow rate of the circuit melt has to be adjusted in such a way that the thermal output required can be removed. The column is equipped with internals, for example trays or structured packings, to increase the separating performance. At the top of the column, an organic solvent having a boiling point smaller than that of PN is introduced. This results in vaporous PN condensing in the upper section of the column and at the same time in the solvent evaporating. This ensures that virtually no PN is discharged via the top of the quench column. The bottom effluent consists of PN with small fractions of the solvent, and also secondary components from the ammoxidation. The low-boiling secondary components may be removed in a subsequent distillation stage. However, preference is given to conveying the melt to the hydrogenation without further low boiler removal.

Hydrogenation:

The phthalonitrile melt or solution or emulsion obtained as described above after the low boiler removal is subsequently fed to the hydrogenation.

In the process according to the invention, there is no removal of high boilers, i.e. of products having a boiling point higher than phthalonitrile (at the same pressure) before the hydrogenation of the PN.

For the hydrogenation of the phthalonitrile to the corresponding xylylenediamine (o-, m- or p-xylylenediamine), particular preference is given to adding ammonia, preferably in liquid form, to the PN.

For the hydrogenation of the phthalonitrile, it is also possible to add an organic solvent. When the hydrogenation is carried out in the presence of ammonia and an organic solvent, preference is given to first preparing the solution or suspension in the solvent.

Preferred solvents here are NMP, xylene, benzylamine, o-, m- or p-methylbenzylamine, xylylenediamine and mixtures thereof.

A preferred embodiment consists in the sole use of liquid ammonia as the solvent.

The weight ratio in the fresh feed of dinitrile to ammonia used is generally from 1:0.15 to 1:15, preferably from 1:0.5 to 1:10, more preferably from 1:1 to 1:5.

For the hydrogenation, the catalysts and reactors (for example fixed bed or suspension method), and also processes (continuous, semicontinuous, batchwise), which are known to those skilled in the art for this reaction may be employed.

In the fixed bed catalyst method, both the liquid phase and the trickle method are possible. Preference is given to a trickle method.

In this regard, reference is made, for example, to the processes described in the applications GB-A-852,972 (equivalent: DE-A-11 19 285) (BASF AG) and DE-A-12 59 899 (BASF AG) and to the U.S. Pat. No. 3,069,469 (California Research Corp.).

The hydrogenation reactor may be operated in straight pass. Alternatively, a circulation method is also possible, in which a portion of the reactor effluent is recycled to the reactor inlet, preferably without preceding workup of the circulation stream. This allows optimum dilution of the reaction solution to be achieved, which has a favorable effect on the selectivity. In particular, the circulation stream may be cooled in a simple and inexpensive manner by means of an external heat transferor, and the heat of reaction thus removed. The reactor can also be operated adiabatically, in which case the temperature rise of the reaction solution may be limited by the cooled circulation stream. Since the reactor itself then does not have to be cooled, a simple and inexpensive design is possible. An alternative is a cooled tube bundle reactor.

Preference is given to catalysts which comprise cobalt and/or nickel and/or iron, as an unsupported catalyst or on an inert support.

The reaction temperatures are generally from 40 to 150° C., preferably from 40 to 120° C.

The pressure is generally from 40 to 300 bar, preferably from 100 to 200 bar.

Isolation of the XDA:

After the hydrogenation, any solvent used and any ammonia used are distilled off.

Preference is given to purifying the xylylenediamine by distilling off relatively low-boiling by-products (at the same pressure) via the top and removing relatively high-boiling impurities via the bottom by distillation.

Particular preference is given to the method in which, after the hydrogenation, any solvent used, any ammonia and also any relatively low-boiling by-products are distilled off via the top and, afterwards, relatively high-boiling impurities are removed from the xylylene by distillation via the bottom.

In a particular embodiment, the removal of relatively low-boiling and relatively high-boiling by-products may also be effected in a sidestream or dividing wall column, in which case pure xylylenediamine may be obtained via a liquid or gaseous sidestream.

Depending on the desired purity, the product (XDA) is additionally extracted with an organic solvent, preferably an aliphatic hydrocarbon, in particular a cycloaliphatic hydrocarbon, very particularly cyclohexane or methylcyclohexane.

This purification by extraction may be effected, for example, according to DE-A-1 074 592.

A schematic overview of a preferred embodiment of the process according to the invention is given by FIG. 1 in the appendix.

The optional process features, 'organic solvent in the hydrogenation' and 'extractive XDA purification' are indicated by dashed lines.

EXAMPLES

Example 1

Figure 1:
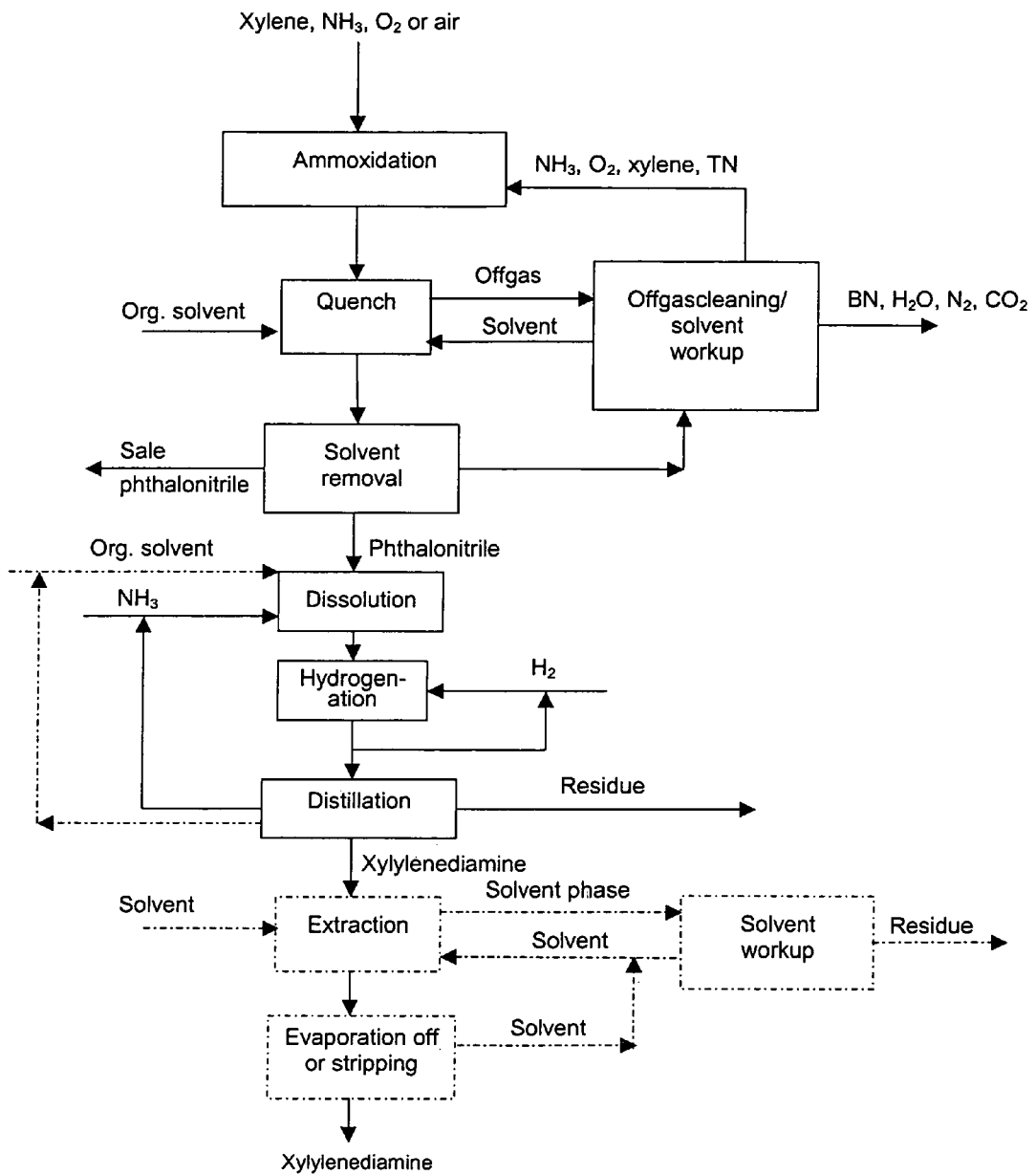
Figure 2:
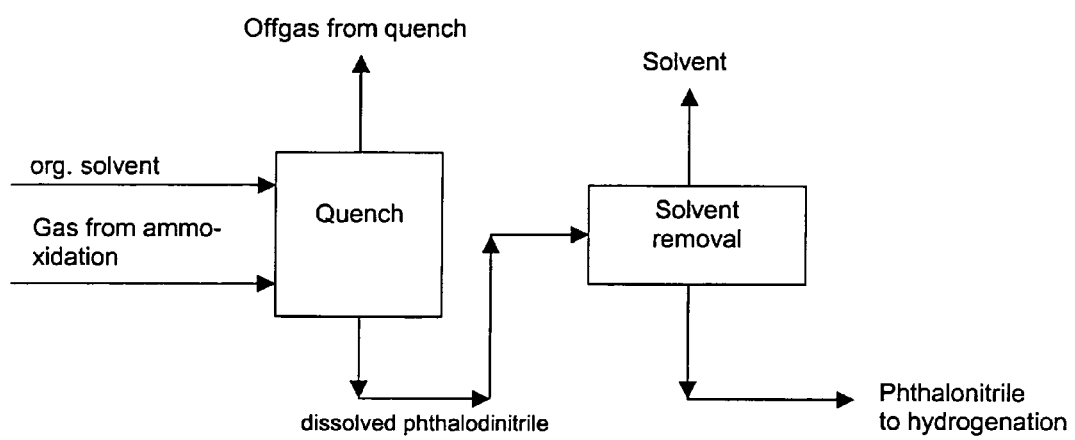
FIG. 2 shows a scheme of the quench step with subsequent low boiler removal (including quench solvent).
Figure 3:
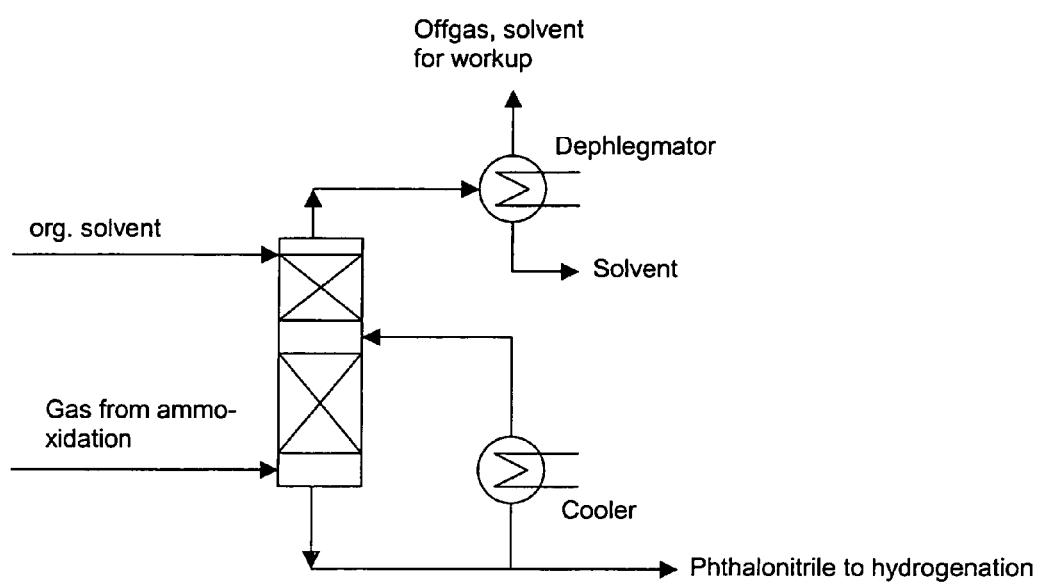
FIG. 3 shows a scheme of the combination of the quench step with the low boiler removal (including quench solvent) in a column.

Ammoxidation of m-xylene, Subsequent Quenching of the Reaction Gases with Tolunitrile as a Solvent, Low Boiler Removal and Hydrogenation of the IPN Formed in the Ammoxidation Stage (cf. Process Scheme in FIG. 1)

A catalyst having the composition $V_4Sb_3W_{0.4}Cs_{0.2}$ on steatite was installed into a tubular reactor as a fixed bed. The apparatus was heated externally to 400° C. Evaporated m-xylene, gaseous ammonia, air and nitrogen were introduced to the reactor ($NH_3$/ m-xylene=8 mol/1 mol; $O_2$/m-xylene=4 mol/1 mol). The furthest upstream part of the reactor was filled with an inert bed, so that the starting materials reached the reaction zone premixed and preheated to 400° C. In the reactor there was a slightly elevated pressure of from 20 to 30 mbar. The hotspot temperature reached 450° C. After conversion (C) of m-xylene of 79%, a selectivity (S) for IPN of 68% was achieved.

The gas mixture leaving the reactor is quenched in a column with tolunitrile. A solution of IPN in tolunitrile is discharged from the quench column at 120° C. and comprises 1% by weight of m-xylene, 0.3% by weight of water, 0.1% by weight of benzonitrile, 80% by weight of tolunitrile and 18.7% by weight of IPN. Unconverted reaction gases and inert gases, and also unconverted m-xylene and a little tolunitrile, are withdrawn in gaseous form via the top of the quench column. This gas may be worked up, in order to recycle the materials of value (in particular $NH_3$, m-xylene, and tolunitrile) into the reaction stage or into the quench circuit. Inerts and secondary components ($H_2O$, benzonitrile, $N_2$, $CO_2$, etc.) are discharged from the workup stage.

The solution of IPN in tolunitrile obtained after the quench is fed at 100 mbar (abs.) to one of the middle stages of a distillation column. Xylene, tolunitrile, benzonitrile and water are removed via the top at 57° C. IPN having 0.1% by weight of tolunitrile is withdrawn via the bottom at 195° C. The top withdrawal stream may be worked up and recycled to the ammoxidation or to the quench circuit.

27% by weight of IPN were mixed with 73% by weight of NMP and hydrogenated in a continuously operated 70 ml tubular reactor over an unsupported cobalt catalyst at 80° C. and 190 bar. Every hour, 70 g of IPN solution and 90 g of ammonia were passed over the catalyst. The yield of MXDA was 96% based on IPN used.

In a subsequent batch distillation, first ammonia which was still dissolved and then NMP and low-boiling secondary components were removed. After removal of the high-boiling impurities, MXDA was obtained in a purity of more than 99.9% by weight.

Example 2 (Alternative Hydrogenation Conditions)

A mixture consisting of 27% by weight of IPN and 73% by weight of NMP, which was mixed together from the pure components, was hydrogenated in a continuous 70 ml tubular reactor over an unsupported cobalt catalyst at 80° C. and 190 bar. Every hour, 70 g of IPN solution and 54 g of ammonia were passed over the catalyst. The same volume flow rate is recycled as a solvent. The yield of MXDA was 95.5% based on IPN used.

Example 3 (Alternative Hydrogenation Conditions)

A mixture consisting of 15% by weight of IPN and 85% by weight of MXDA, which was mixed together from the pure components, was hydrogenated in a continuous 70 ml tubular reactor over an unsupported cobalt catalyst at 60° C. and 190 bar. Every hour, 117 g of IPN solution and 150 g of ammonia were passed over the catalyst. A quarter of the volume flow rate is recycled as a solvent. The yield of MXDA was 92% based on IPN used.

In subsequent distillation steps, first ammonia and then low-boiling secondary components were removed. After removing the high-boiling impurities via the bottom, MXDA was obtained as a top product of a distillation column in a purity of more than 99.9% by weight.

Example 4 (Alternative Hydrogenation Conditions)

30 g of IPN and 5 g of Raney nickel were initially charged in a stirred autoclave. After 66 g of ammonia had been added, 50 bar of hydrogen were injected and the autoclave was heated to 100° C. Injection of further hydrogen maintained an overall pressure of 100 bar for 5 hours. The conversion of IPN was quantitative, and a yield of 94% based on IPN used was obtained.

(The data of the quench step and purifying distillation of IPN reported above are the results of a thermodynamic simulation. In this simulation, the quench was considered to be an apparatus in which there is thermodynamic equilibrium between gas and liquid phase. In addition to the pure material data of the components involved, real binary data were used in the calculation. Such calculations can be carried out with commercial calculation programs, here: Aspen Plus, which are familiar to those skilled in the art).

Example 5

Investigations of Solubility of IPN in Different Solvents

The solubility of IPN in NMP is approx. 26% by weight at 60° C. and approx. 41% by weight at 90° C.

At 90° C., pseudocumene attains a solubility of only 20% by weight and mesitylene of only 12% by weight.

At 60° C., the solubility of IPN in mesitylene or pseudocumene is in each case below 10% by weight.

Example 6

A catalyst of the composition $V_4Sb_3K_{0.4}Ba_{0.2}$ on steatite was installed into a tubular reactor as a fixed bed. The apparatus was heated to 415° C. externally. Evaporated m-xylene, gaseous ammonia and air were fed to the reactor ($NH_3$/m-xylene=14 mol/1 mol; $O_2$/m-xylene=4 mol/1 mol). The catalyst of the first half of the reactor was diluted with 70% by weight of steatite spheres, the second half with 40% by weight. In the reactor, there was a slightly elevated pressure of 0.02 bar. The hotspot temperature reached 430° C. At a conversion of m-xylene of 88%, a selectivity for IPN of 71% was obtained.

The hot quench gas is fed to the bottom of a quench column. In the lower section of the column, a melt of IPN is circulated through a heat exchanger and fed back to the 4th theoretical plate of the column at a temperature of 165° C. At the top of the column, fresh m-tolunitrile is fed at 20° C. The IPN is absorbed by the circulating melt and discharged via the bottom at 198° C. with a purity of more than 99% by weight. The secondary components present are m-xylene (640 ppm by weight), water (0.15% by weight) and 0.55% by weight of m-tolunitrile. In the upper section, the gas mixture ascending from the lower section of the column is washed in countercurrent with tolunitrile, and the IPN is fully condensed. The reaction gases from the ammoxidation are discharged in gaseous form together with the m-tolunitrile solvent at 140° C. via the top. This gas stream comprises virtually no IPN. The melts discharged via the bottom may be used directly for hydrogenation.

(The reported data of the quench step are the results of a thermodynamic simulation as described above).

We claim:

1. A process for preparing ortho-, meta- or para-xylylenediamine, comprising the steps of:
   ammoxidizing ortho-, meta- or para-xylene to o-phthalonitrile iso- or terephthalonitrile and hydrogenating the phthalonitrile,
   which comprises contacting the vaporous product of the ammoxidation stage directly with a liquid organic solvent, which has a lower boiling point than the phthalonitrile, or with molten phthalonitrile (quench),
   removing components having a boiling point lower than phthalonitrile (low boilers) from the resulting quench solution or suspension or phthalonitrile melt,
   before the hydrogenation of the phthalonitrile, not removing any products having a boiling point higher than phthalonitrile (high boilers) and
   carrying out the hydrogenation in the absence of an organic solvent.

2. The process according to claim 1, comprising the steps of ammoxidizing meta-xylene to isophthalonitrile and hydrogenating the isophthalonitrile in order to prepare meta-xylylenediamine.

3. The process according to claim 1, wherein the liquid organic solvent used for the quench is an aromatic hydrocarbon, a heterocyclic compound, an aromatic nitrile and/or a heterocyclic nitrile.

4. The process according to claim 1, wherein the liquid organic solvent used for the quench is tolunitrile, benzonitrile and/or N-methyl-2-pyrrolidone (NMP).

5. The process according to claim 1, wherein, in the quench with a liquid organic solvent, the temperature of the quench effluent is from 40 to 180° C., and, in the quench with molten phthalonitrile, the temperature of the quench effluent is from 165 to 220° C.

6. The process according to claim 1, wherein the low boilers are partly or fully removed from the resulting quench solution or suspension or phthalonitrile melt by distillation via the top, while phthalonitnle is removed via the bottom together with products having a boiling point higher than phthalonitrile (high boilers).

7. The process according to claim 1, wherein the quench of the vaporous product of the ammoxidation stage is carried out in a column in such a way that reaction gases and low boilers are partly or fully removed via the top and phthalonitrile together with products having a boiling point higher than phthalonitrile (high boilers) are removed via the bottom.

8. The process according to claim 1, wherein the ammoxidation is carried out at temperatures of from 300 to 500° C. over a catalyst comprising V, Sb and/or Cr, as an unsupported catalyst or on an inert support.

9. The process according to claim 1, wherein the hydrogenation is carried out in the presence of ammonia.

10. The process according to claim 1, wherein the hydrogenation is carried out at temperatures of from 40 to 150° C. over a catalyst comprising Ni, Co and/or Fe, as an unsupported catalyst or on an inert support.

11. The process according to claim 1, wherein, after the hydrogenation, the xylylenediamine is purified by distilling off any solvent used and ammonia, and also any relatively low-boiling by-products, via the top and distillatively removing relatively high-boiling impurities via the bottom.

12. The process according to claim 1, wherein, after the hydrogenation, any solvent used and ammonia, and also any relatively low-boiling by-products, are distilled off via the top and, afterwards, any relatively high-boiling impurities are removed from the xylylenediamine by distillation via the bottom.

13. The process according to claim 11, wherein the xylylenediamine, after the distillation, is extracted for further purification with an organic solvent.

14. The process according to claim 13, wherein cyclohexane or methylcyclohexane is used for the extraction.

15. The process according to claim 2, wherein the liquid organic solvent used for the quench is an aromatic hydrocarbon, a heterocyclic compound, an aromatic nitrile and/or a heterocyclic nitrile.

16. The process according to claim 2, wherein the liquid organic solvent used for the quench is tolunitrile, benzonitrile and/or N-methyl-2-pyrrolidone (NMP).

17. The process according to claim 2, wherein, in the quench with a liquid organic solvent, the temperature of the quench effluent is from 40 to 180° C., and, in the quench with molten phthalonitrile, the temperature of the quench effluent is from 165 to 220° C.

18. The process according to claim 3, wherein, in the quench with a liquid organic solvent, the temperature of the quench effluent is from 40 to 180° C., and, in the quench with molten phthalonitrile, the temperature of the quench effluent is from 165 to 220° C.

19. The process according to claim 2, wherein, in the quench with a liquid organic solvent, the temperature of the quench effluent is from 40 to 180° C., and, in the quench with molten phthalonitrile, the temperature of the quench effluent is from 165 to 220° C.

20. The process according to claim 2, wherein the low boilers are partly or fully removed from the resulting quench solution or suspension or phthalonitrile melt by distillation via the top, while phthalonitrile is removed via the bottom together with products having a boiling point higher than phthalonitrile (high boilers).

* * * * *